(12) United States Patent
Datta

(10) Patent No.: US 8,313,473 B2
(45) Date of Patent: Nov. 20, 2012

(54) DIAPER STRUCTURE WITH ALIGNMENT INDICATOR

(75) Inventor: Paul Joseph Datta, Appleton, WI (US)

(73) Assignee: Kimberly-Clark Worldwide, Inc., Neenah, WI (US)

(*) Notice: Subject to any disclaimer, the term of this patent is extended or adjusted under 35 U.S.C. 154(b) by 224 days.

(21) Appl. No.: 12/704,270

(22) Filed: Feb. 11, 2010

(65) Prior Publication Data
US 2010/0147722 A1 Jun. 17, 2010

Related U.S. Application Data

(62) Division of application No. 10/880,882, filed on Jun. 30, 2004, now Pat. No. 7,842,849.

(51) Int. Cl.
A61F 13/15 (2006.01)
A61F 13/20 (2006.01)

(52) U.S. Cl. ............................ 604/385.02; 604/385.09

(58) Field of Classification Search .............. 604/361, 604/378–380, 385.09
See application file for complete search history.

(56) References Cited

U.S. PATENT DOCUMENTS

| 4,673,403 | A | 6/1987 | Lassen et al. | |
|---|---|---|---|---|
| 5,468,236 | A | 11/1995 | Everhart et al. | |
| 5,776,123 | A | 7/1998 | Goerg et al. | |
| 6,315,765 | B1 | 11/2001 | Datta et al. | |
| 6,601,706 | B2 | 8/2003 | McManus et al. | |
| 2003/0070955 | A1* | 4/2003 | Kuske et al. | 206/494 |
| 2003/0158532 | A1* | 8/2003 | Magee et al. | 604/385.01 |
| 2003/0199845 | A1 | 10/2003 | Roe et al. | |
| 2004/0097896 | A1 | 5/2004 | Raufman et al. | |
| 2004/0176736 | A1 | 9/2004 | Christon et al. | |
| 2004/0186448 | A1 | 9/2004 | Misek et al. | |
| 2005/0096612 | A1 | 5/2005 | Davis et al. | |
| 2005/0145523 | A1 | 7/2005 | Zander et al. | |
| 2006/0004337 | A1 | 1/2006 | Datta | |

FOREIGN PATENT DOCUMENTS

EP 1330224 6/2004

* cited by examiner

*Primary Examiner* — Melanie Hand
(74) *Attorney, Agent, or Firm* — Dority & Manning, P.A.

(57) ABSTRACT

An absorbent garment, such as a diaper structure, includes a visually discernible alignment indicator visible from a body-facing surface. The alignment indicator includes at least one first reference point. The absorbent garment comes with instructions defining the location of the first reference point on the absorbent article, defining the location of a second reference point on a wearer, and instructing the consumer to position the absorbent garment so that the first reference point optically aligns with the second reference point, and to fasten the absorbent garment in the position.

5 Claims, 8 Drawing Sheets

DIAPER STRUCTURE WITH ALIGNMENT INDICATOR

CROSS-REFERENCE TO RELATED APPLICATIONS

The present application is a divisional of application Ser. No. 10/880,882filed Jun. 30, 2004.

BACKGROUND OF THE INVENTION

This invention is directed to a diaper structure having an alignment indicator for optimal donning and fit, and a method of donning a diaper structure. Examples of diaper structures include infant diapers, toddler diapers, adult-sized diapers, swimwear and the like which require assembly, adjustment and/or alignment of the front and rear waistband regions, and fastening during donning.

Diaper structures are designed to provide comfortable fit, high absorbency, and optimal leakage protection. Typical diaper structures include a chassis having a front waist region, a back waist region, crotch region, and fastenable side panels extending from at least one of the front and back waist regions. The chassis typically includes a liquid-permeable body side liner, a liquid-impermeable outer cover, and an absorbent core between them. A surge layer may be present between the body side liner and absorbent core. A dampness-inhibiting spacer layer may be present between the absorbent core and outer cover. Elasticized waistbands and leg bands may also be associated with one or both waistband regions or at least partially around the leg openings, respectively.

To achieve the optimal combination of comfortable fit, absorbency and leakage protection, the caregiver is encouraged to don the diaper structure on the wearer so that the front and rear waist regions are substantially aligned with each other. For some diaper structures, the optimal properties may be achieved by perfect alignment of the front and rear waist regions. For many diaper structures, the optimal properties are achieved by aligning the waistband regions so that the front waist edge is slightly below the back waist edge relative to a standing wearer. For the caregiver, it has often been difficult to place the diaper structure under the baby or other wearer and fasten it to achieve optimal alignment, without multiple attempts. Often, the caregiver fastens the diaper structure on the wearer and then discovers that the waistband regions are not optimally aligned. The caregiver must then unfasten the diaper structure, reposition it, and fasten it again until optimal alignment is achieved.

Similarly, the caregiver is encouraged to don the diaper structure on the wearer so that the center of the back waistband and the center of the front waistband align with the center of the child's back and stomach. The encouraged side-to-side alignment keeps the leg elastics equally tight on the child's legs, thus preventing irritation on one side and leakage on the other side. More particularly, if the diaper is cocked to one side or the other side, the size of the leg holes is disproportionate. The leg elastics then apply unequal tension, resulting in one side that is tight and the other side that is loose.

SUMMARY OF THE INVENTION

The present invention is a diaper structure having at least one alignment indicator that provides a visually distinguishable first reference point or an inferred point centered between two references on the diaper structure. The alignment indicator can be a distinct color, pattern, texture or other feature which visually distinguishes the reference point from the surrounding area on the diaper structure. The alignment indicator is suitably visible from the body-facing side of the diaper structure prior to applying the diaper structure to the wearer. Consequently, the alignment indicator is not intended for use in pre-fastened garments that are exclusively pull-on garments. The indicator is suitably provided on the body-facing side of the diaper structure, or on a layer which is visible from the body-facing side.

The first reference point provided by the alignment indicator is positioned to optically align with a second reference point defined on the body of the wearer. In one instance, the second reference point may be defined as the upper end of the crevice separating the wearer's buttocks. In this instance, the alignment indicator may be positioned in a laterally central position on the chassis, longitudinally inward from the rear waist edge at a point which is intended to optically align with a second reference point on the wearer, for example the upper end of the wearer's crevice. In another instance, the second reference point may be a point on a baby or other wearer which is barely visible from above when the wearer is lying in a diaper-changing position as the diaper structure is being donned. In this instance, the alignment indicator may be an edge of a colored surge material, or an edge of a color patch on a body side liner, which is barely visible from above when the diaper structure is properly positioned underneath the wearer.

During donning of the diaper structure, the caregiver positions the diaper structure so that the first reference point defined by the alignment indicator optically aligns with the second reference point on the wearer. By optically aligned, it is meant that the caregiver's eye is nearly vertical over the wearer, and lines up the first reference point on the diaper with the visible position of the second reference point on the wearer. The alignment indicator is positioned on the diaper structure such that when the first reference point aligns with the second reference point, and the diaper structure is closed and fastened, the front and rear waist regions will be optimally aligned.

The invention may also include second and third alignment indicators that help the caregiver align the diaper from side to side. In such an embodiment, the caregiver grasps near or on the second indicator and guides it under the wearer to align with the center of the back. This is done instinctively, or by feel rather than by sights, so the caregiver can optically focus on aligning the first alignment indicator. The third alignment indicator is also grasped and the diaper is then folded so that the third alignment indicator is moved toward and/or over the belly button.

The present invention is also directed to a method of donning an absorbent garment on a wearer. The method includes the steps of defining one or more first reference points on the absorbent garment, defining one or more second reference points on a wearer, placing the absorbent garment in a position relative to the wearer where the first reference point optically aligns with the second reference point, and fastening the absorbent garment in the position.

DEFINITIONS

Figure 1:
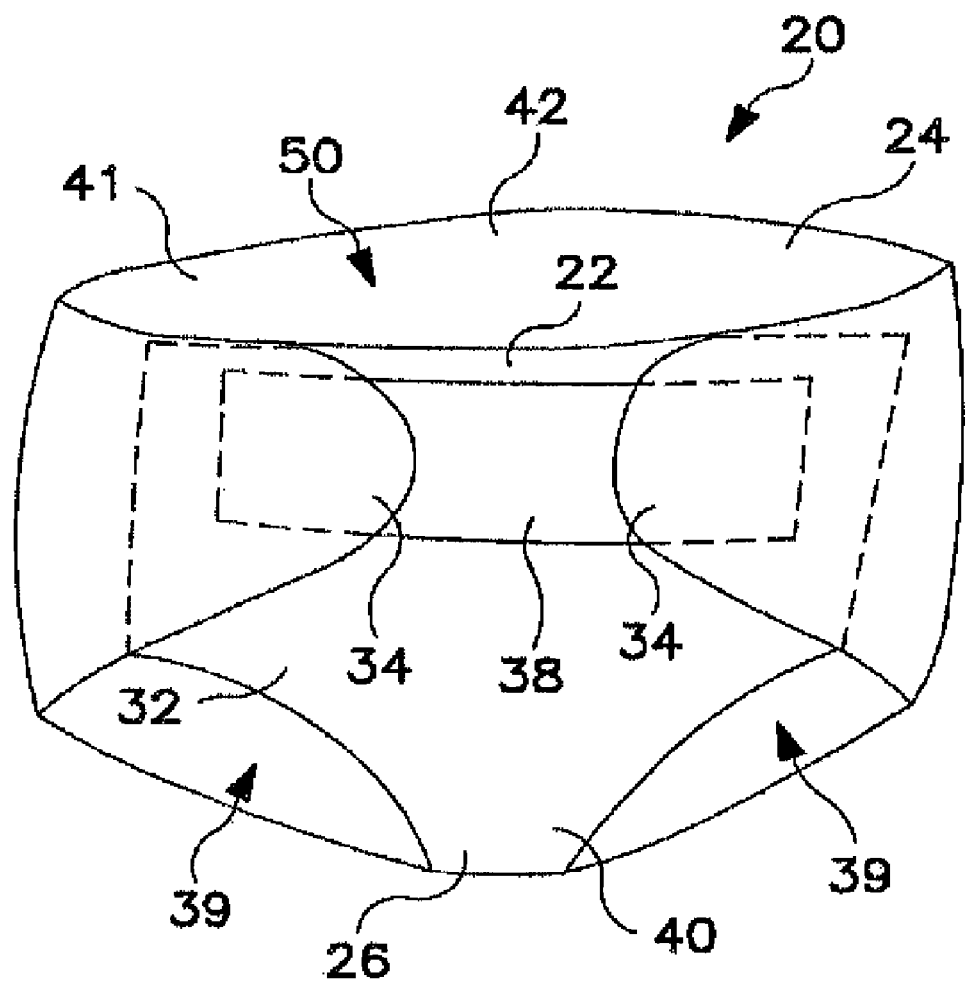
FIG. 1 is a perspective view of a diaper structure, in a fastened position with front and back waistband regions in perfect alignment.

Within the context of this specification, each term or phrase below will include the following meaning or meanings.

"Absorbent garment" includes personal care garments, medical garments, and the like. The term "disposable garment" includes garments that are typically disposed of after 1-5 uses. The term "personal care garment" includes diapers, diaper pants, training pants, swimwear, absorbent underpants, adult incontinence products, feminine hygiene products, and the like. The term "diaper structure" refers to articles that can be assembled on a wearer by securing fasteners when the garment is in place on a wearer, as opposed to pre-fastened pull-on garments.

"Aligned" refers to a lateral alignment of a front waist region and a back waist region when a diaper structure is fastened on a wearer. "Optimal alignment" means the front and back waist regions are aligned so as to provide optimal fit, absorbency and leakage protection. "Perfect alignment" means the front and back waist regions are aligned so that the front waist edge and back waist edge are aligned. While optimal and perfect alignment may coincide, an optimal alignment often results when the front waist edge is slightly below the back waist edge relative to a standing wearer.

"Longitudinally aligned" refers to a longitudinal alignment of the front waist region with the plane of symmetry that divides the left and right sides of the wearer, and a longitudinal alignment of the back waist region with the same left/right plane of symmetry, when a diaper structure is fastened on the wearer. "Optimal longitudinal alignment" means the left and right front side panels extend an equal distance from the left/right symmetry plane of the wearer, and left and right back side panels also extend an equal distance from the left/right symmetry plane of the wearer. This optimal longitudinal alignment assures an equal amount of diaper material overlap on each side of the wearer.

"Attached" refers to the joining, adhering, connecting, bonding, or the like, of at least two elements. Two elements will be considered to be attached together when they are attached directly to one another or indirectly to one another, such as when each is directly attached to intermediate elements.

"Diaper structure" refers to an absorbent garment having a front waist region and a back waist region, in which manual adjustment and fastening are required to align the front waist region relative to the back waist region on a wearer. The term does not include absorbent garments in which the front and back waist regions are permanently aligned in a fixed position by pre-attached side panel connections, and cannot be manually adjusted relative to each other.

"Fastened" refers to a manual attachment wherein the front and rear waist regions are manually adjusted relative to each other and fastened in a selected aligned position.

"Fold line" refers to a crease resulting from one section of a continuous object folded onto another section of the same object. Insignificant wrinkles are not considered to constitute fold lines.

"Longitudinal" and "transverse" have their customary meaning, as indicated by the longitudinal and transverse axes depicted in FIGS. 2-5. The longitudinal axis lies in the plane of the article and is generally parallel to a vertical plane that bisects a standing wearer into left and right body halves when the article is worn. The transverse axis lies in the plane of the article generally perpendicular to the longitudinal axis.

"Nonwoven" and "nonwoven web" refer to materials and webs of material having a structure of individual fibers or filaments which are interlaid, but not in an identifiable manner as in a knitted fabric. The terms "fiber" and "filament" are used herein interchangeably. Nonwoven fabrics or webs have been formed from many processes such as, for example, meltblowing processes, spunbonding processes, air laying processes, and bonded carded web processes. The basis weight of nonwoven fabrics is usually expressed in ounces of material per square yard (osy) or grams per square meter (gsm) and the fiber diameters are usually expressed in microns. (Note that to convert from osy to gsm, multiply osy by 33.91.)

"Tactically discernible" refers to an indicator that can be detected or perceived by any of the five senses, namely sight, touch, sound, smell, and/or taste.

DESCRIPTION OF PREFERRED EMBODIMENTS

In accordance with one embodiment of the invention, a diaper structure has an alignment indicator for optimal alignment of the front and back waist regions relative to each other and the wearer. For ease of explanation, the diaper structure described below is an infant diaper.

Referring to FIG. 1, a diaper 20 is illustrated in a fastened position as the garment would appear when worn. FIGS. 2-5 illustrate the diaper 20 in a stretched flat state with the layers separated in an exploded view for clarity. The diaper 20 includes an absorbent chassis 32 defining a front waist region 22, a back waist region 24, and a crotch region 26 interconnecting the front and back waist regions. In the fastened position, the absorbent chassis 32 defines a three-dimensional pant configuration having a waist opening 50 and a pair of leg openings 39. The chassis 32 includes a body side liner 42 which is configured to contact the wearer, and an outer cover 40 opposite the body side liner which is configured to contact the wearer's clothing. An absorbent core 44 (FIG. 2) is positioned or located between the outer cover 40 and the body side liner 42. The absorbent core 44 has a shorter length and width than the outer cover 40 and body side liner 42 and is spaced inboard from all edges of the outer cover 40 and body side liner 42. A surge layer 43, placed between the body side liner 42 and absorbent core 44, facilitates rapid transfer and distribution of liquid to the absorbent core 44.

The front waist region 22 includes the portion of the diaper 20 which, when worn, is positioned on the front of the wearer while the back waist region 24 includes the portion of the diaper which, when worn, is positioned on the back of the wearer. The crotch region 26 of the diaper 20 includes the portion of the diaper which, when worn, is positioned between the legs of the wearer and covers the lower torso of the wearer. The regions 22, 24 and 26 may be defined as each encompassing about one-third of the length of the diaper 20; however, either waist region may encompass as little as 10% of the diaper length. For purposes of locating waist area indicators, the front and/or back waist regions may be restricted to about 20% of the diaper length, or about 10% of the diaper length.

The waist regions 22, 24 are configured to encircle the waist of the wearer when the diaper 20 is worn. Portions of the materials in the back waist region 24 may overlap the materials in the front waist region 22, or vice-versa, when the diaper is assembled to encircle the legs and waist of the wearer. A longitudinal length of the absorbent chassis 32 is the distance between (and including) the front waist region 22 and the back waist region 24. The longitudinal length is measured parallel to the longitudinal axis. For reference, arrows 48 and 49 depicting the orientation of the longitudinal axis and the transverse axis, respectively, of the diaper 20 are illustrated in FIGS. 2-5.

The illustrated outer cover 40 has elastic waist bands 52 and 54 disposed adjacent to or near the front waist edge 51 and rear waist edge 53, respectively, and elastic leg bands 56 and 58 disposed adjacent to lateral side edges 55 and 57, respectively. Side panels 34 laterally extend from the back waist region 24 of outer cover 40. The side panels 34 may be extensions of the outer cover material 40 or the body side liner material 42, or may be a separate material attached to the outer cover 40 or the body side liner 42, or may be sandwiched between the outer cover 40 and the body side liner 42. Fastener tabs 36 disposed on side panels 34 are adapted for engagement with landing member 38 on the front waist region 22 of the diaper (FIG. 1), when the diaper is closed. The fastener tabs 36 may be hook-and-loop type fasteners, adhesive tape tabs, or other suitable fasteners. Fasteners are used to assemble and hold the diaper in a pant configuration.

The diaper structure of the invention includes an alignment indicator 75. The alignment indicator 75 may be a mark, a line, an internal feature or an internal layer of the diaper structure, beneath the body side liner. In the diaper structure of FIG. 2, the alignment indicator 75 is a visible internal feature, namely a rear edge 71 of surge layer 43, which is visible from the body-facing surface 41 of the diaper structure 20, and through the body side liner 42. The alignment indicator 75 can be made visible by coloring all or part of the surge layer 75 with a contrasting color that is visible through body side liner 42. For instance, if the body side liner 42 is white, and at least an edge of the surge layer 43 is aqua blue, dark blue, green, or another contrasting color, the alignment indicator 75 is visible through the body side liner as a line separating a white region and a colored region appearing at body-facing surface 41. The alignment indicator 75 may precisely identify a particular longitudinal position by viewing the diaper surface. This alignment indicator 75 is positioned while sliding the diaper under the wearer to optically align with a second reference point on the wearer.

The alignment indicator 75 may be in the form of a tactically discernible indicator, such as a contrasting line, spot, circle, texture, or pattern. For example, the alignment indicator 75 may include one or more vertical and/or lateral lines. As another example, the alignment indicator 75 may include a printed region of color. As yet another example, the line of contrast between two colors, such as between a blue front region and a white back region, may be used as an alignment indicator 75. Additionally, side regions could be a third color or a different shade in order to avoid confusion over the location of the alignment indicator 75.

Figure 8:
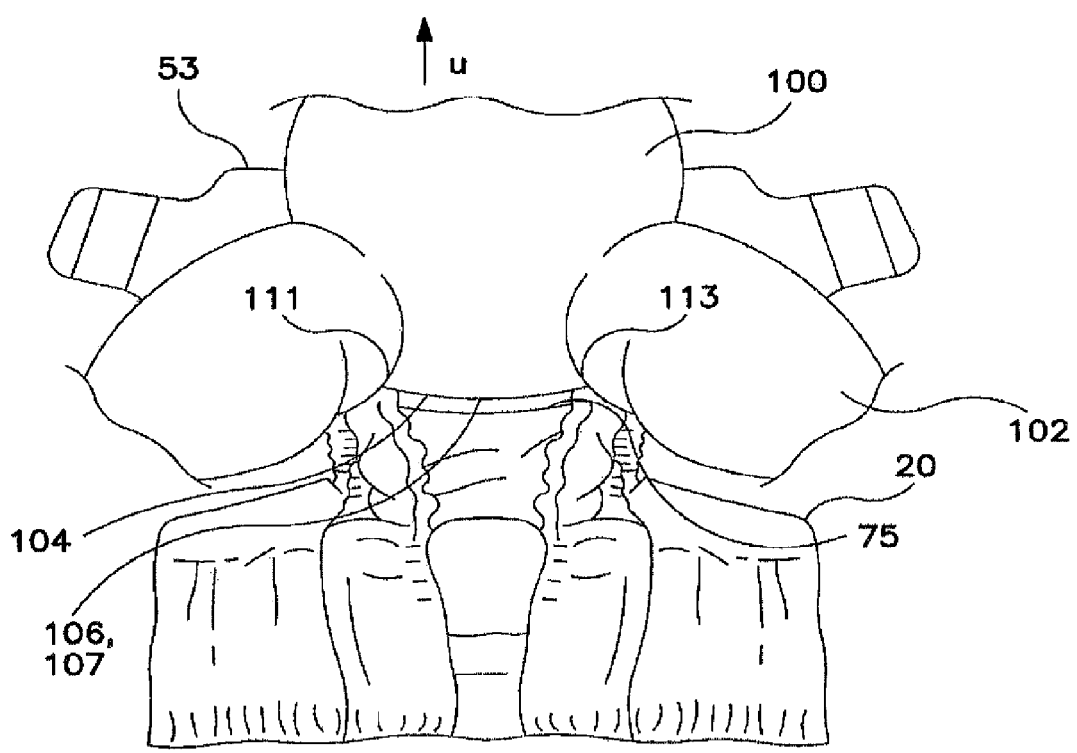
FIG. 8 illustrates a method of donning the diaper structure of FIG. 2 on a wearer.

The alignment indicator 75 includes a first reference point 77 which, during donning of the diaper structure, is positioned to optically align a second reference point on the wearer's body. This principle is illustrated in FIG. 8. A baby 100 is shown in a diaper-changing position, typically on his or her back with legs 102 in the air. During the diaper-changing process, babies often squirm and kick. Caregivers are very concerned with the amount of time it takes to diaper a baby during this active phase. Caregivers want the diaper to go on correctly with excellent fit the first time and do not want to fuss with alignment while diapering and, more importantly, do not want to repeat the activity due to an improper fit the first time. To provide proper alignment, a diaper 20 is positioned partially underneath the baby 100, with its back edge 53 being pushed underneath the baby first. The back edge 53 is pushed or pulled upward in the direction of arrow U until the alignment indicator 75 is barely visible from the viewpoint of the caregiver.

The diaper 20 is properly longitudinally positioned when the alignment indicator 75 optically aligns with the top edge of the baby's buttocks 104 (i.e., the edge closest to the baby's waist), at about the second reference point 107 where the crevice 106 between the buttocks 104 ceases. The diaper 20 is properly laterally positioned when the first reference point 77 (which is the lateral center point of the alignment indicator 75) optically aligns with the second reference point 107. The first reference point 77 is said to "optically align" with the second reference point 107 when the caregiver, when positioned nearly vertical over the wearer, optically aligns the first reference point 77 with the second reference point 107 along a line nearly perpendicular to the body-facing surface 41 of diaper 20. The diaper 20 can then be closed and fastened in its optimal position on the baby.

A diaper structure may include more than one alignment indicator in order to facilitate alignment in the lateral and longitudinal directions, and more clearly define the location of a reference point. In the diaper 20 of FIG. 3, the surge layer 43 is colored as in FIG. 2, and has a back edge 71 defining an alignment indicator 75 which, in turn, includes a first reference point 77 at its center. To better define the location of first reference point 77, a second alignment indicator 79 in the form of a visually discernible line may be printed along a longitudinal axis of body side liner 42. From the viewpoint of the caregiver, the alignment indicator 75 (visible through body side liner 42) may intersect the alignment indicator 79 at the precise location of the first reference point 77. When such a diaper 20 is donned on a wearer as shown in FIG. 8, the diaper 20 will be positioned under the baby 100 and adjusted so that the alignment indicator is barely visible at the back edge of the buttocks 104, and so that the alignment indicator 79 is parallel to the crevice 106 between buttocks 104.

Figure 2:
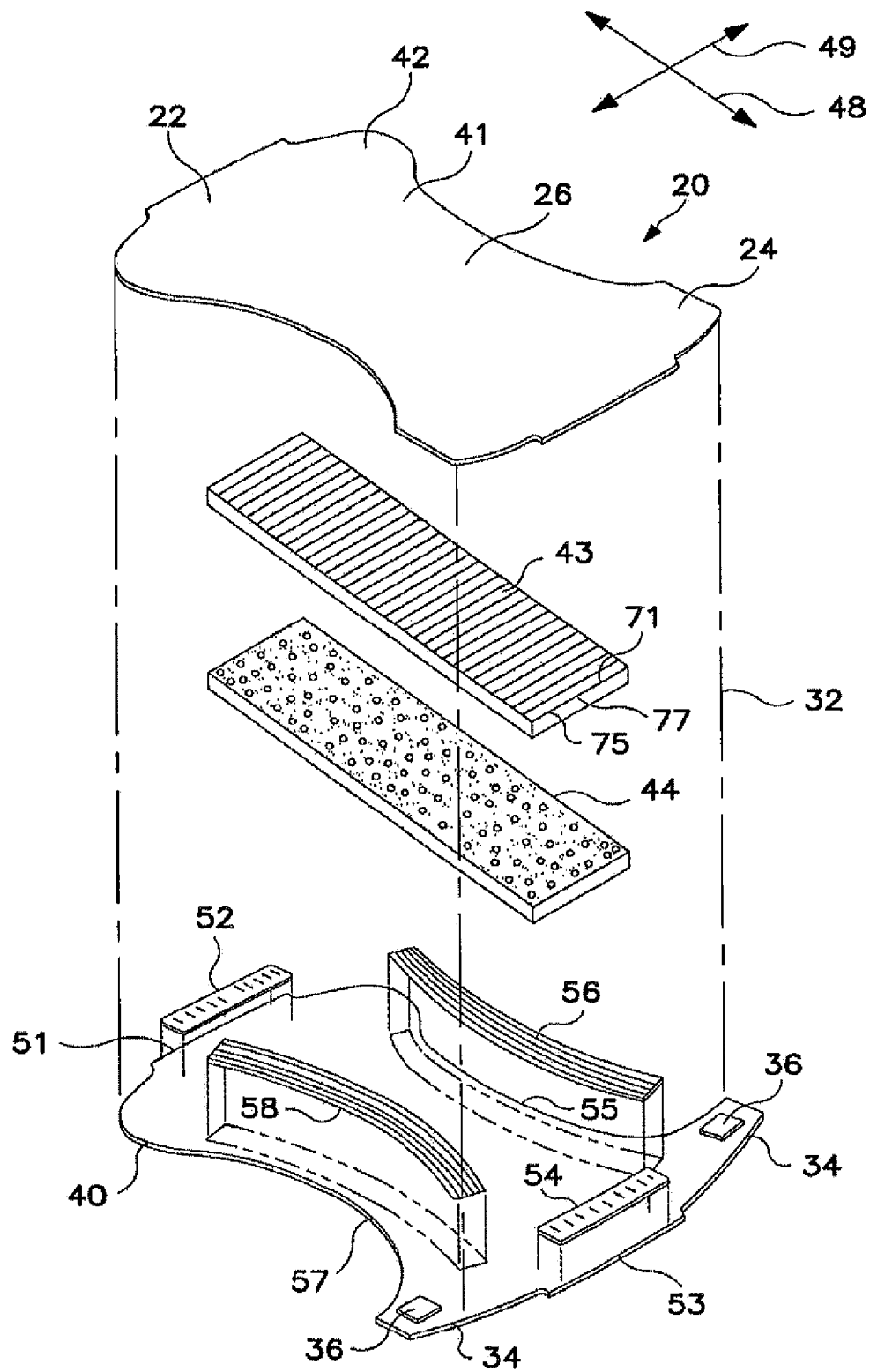
FIGS. 2-5 are exploded views of a diaper structure similar to the diaper structure of FIG. 1 in a stretched flat state, showing the individual layers and different embodiments of the alignment indicator.
Figure 3:
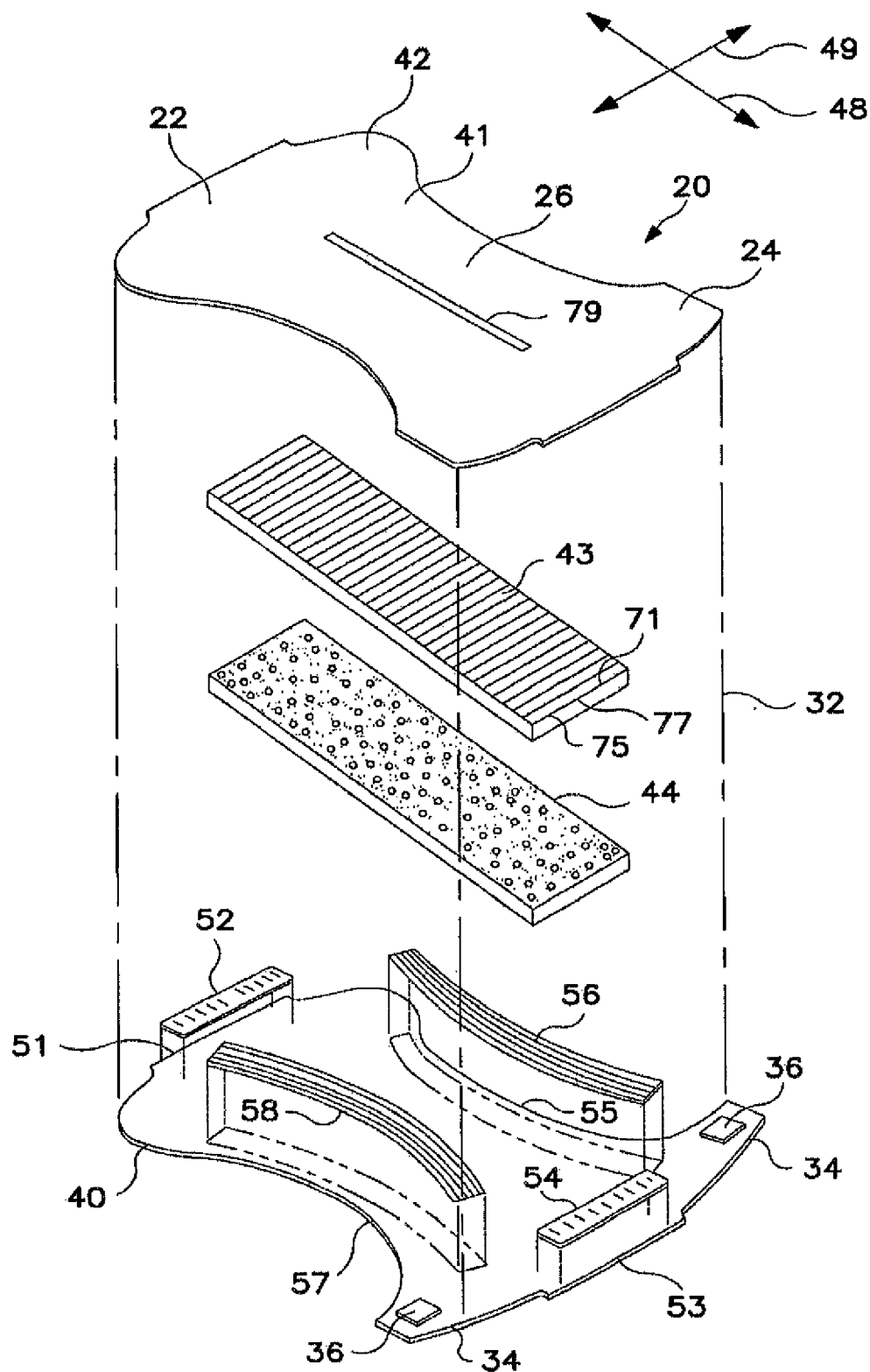
Figure 4:
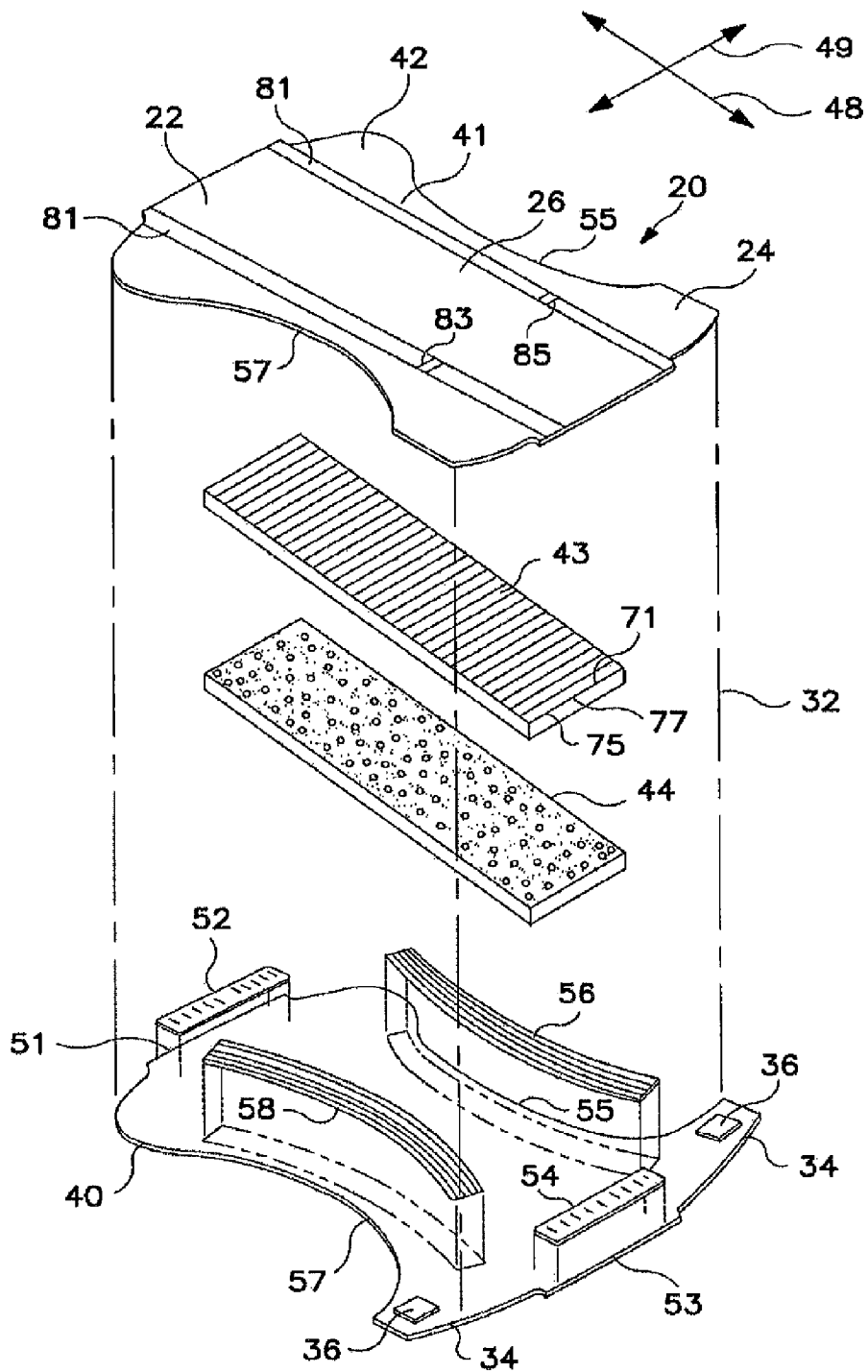
Figure 6:
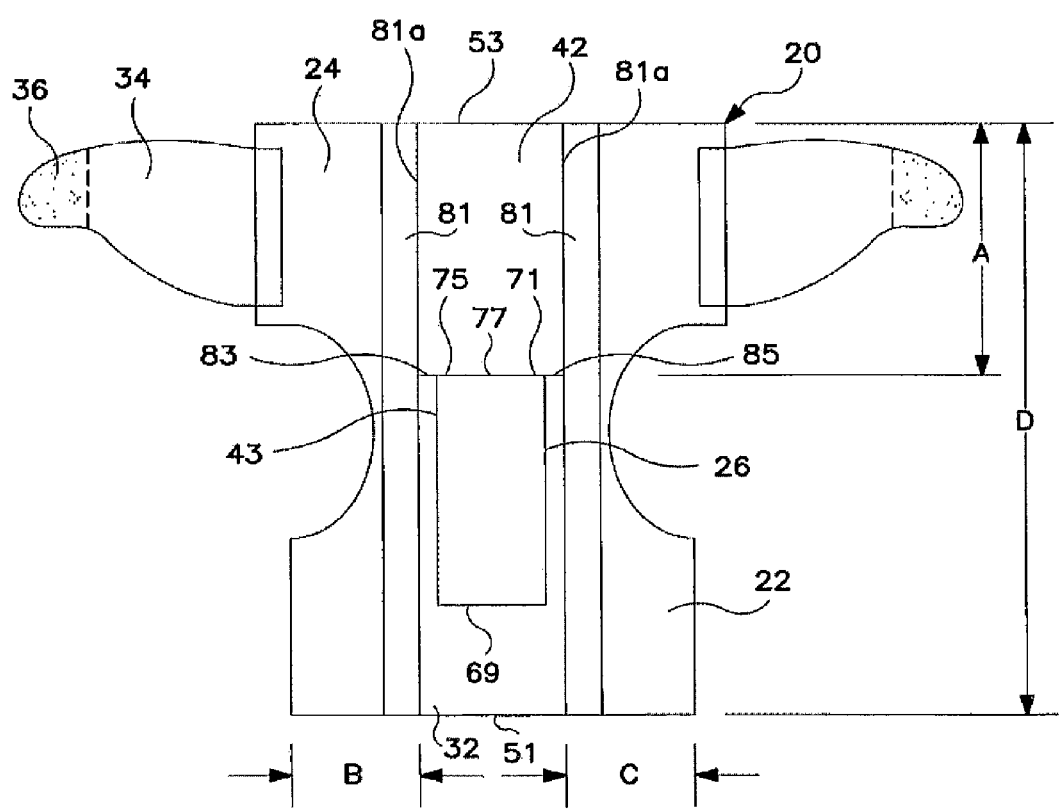
FIG. 6 is a plan view of a diaper structure similar to the diaper structure of FIG. 1 in a stretched flat state, showing the body-facing surface of the diaper structure and illustrating the positioning of alignment indicators.

In the diaper 20 of FIG. 4, the surge layer 43 is colored as in FIG. 2, and has a back edge 71 defining an alignment indicator 75 which, in turn, includes a first reference point 77 at its center. The body side liner 42 includes a pair of transversely opposed alignment indicators in the form of colored bands 81, each longitudinally disposed and visually discernible, and each spaced an equal distance from the nearest side edge 55 or 57 of the diaper. From the viewpoint of the caregiver, the alignment indicator 75 (visible through body side liner 42) will intersect alignment indicators 81 at the locations of the two additional first reference points 83 and 85 shown on the body side liner 42. As shown in FIG. 6, the alignment indicator 75 may have to be extended to intersect the alignment indicators 81 which are shown as the facing edges of the colored bands 83 and 85. In this example shown in FIG. 6, the alignment indicators 75, 81 are discrete, yet are independent indicators that do not create a pattern or have curves. It is preferred that the indicators be discrete to avoid confusion as to the different alignment function of each indicator. One type of alignment indicator 75 functions as a lateral alignment indicator and another type of alignment indicator 81 functions as a longitudinal alignment indicator. Having different colors, different components, and/or discrete locations for the different alignment features provides the benefit of helping the caregiver easily distinguish the difference between the indicators and, thus, speeds up the diapering process.

The diaper structure 20 is donned by first grasping the back waist area and sliding the diaper structure under the baby. This invention uses the second alignment indicators to help assure that the diaper structure 20 is slid in place to laterally align and eliminate any future adjustments of the back waist area. This saves time and frustration while diapering active squirmy babies. The second alignment indicators 81 may be the facing edges of two containment flaps. The caregiver can visualize the longitudinal center line of the diaper as being a line centered between the second alignment indicators 81. By grasping near this line, the caregiver can guide the visualized center line under the wearer. This action can become instinctive to center the diaper laterally by knowing where to grasp near the center of the back waistband. For optimal lateral alignment, the second alignment indicator is slid up the symmetry plane of the baby in a fashion to assure the center of the back waist edge is at the center of the wearer's back.

A line or lines serving as the second alignment indicator may continue for at least one-third the length of the diaper structure. A long line allows continual viewing of the indicator while sliding the diaper structure under the wearer. With squirming babies, adjustments can be made while sliding to deliver optimal fit without secondary adjustments.

Second alignment indicators may be tactical rather than visual, with one example being an embossed area or pattern in the back waist area. The caregiver may then feel where the second alignment indicator is and be able to apply full visual attention to the wearer when grasping the diaper structure 20 for application. The tactical pattern or area may be about 2 inches in width or less. This allows the caregiver to easily find the indicator and eliminates trying to determine the center. The pattern or a portion of the pattern may optimally be less than three-quarters of an inch so that when touched it is easy to determine the center of the diaper at first contact. The second alignment indicator may be on either the outer surface 37, the body-facing surface 41, or both surfaces of the diaper structure 20.

A third alignment indicator may be located on the front of the diaper and again may also be tactical. The third alignment indicator is used when folding the diaper on the baby. By using the third alignment indicator to identify the center of the front waist band area, the caregiver can fold the front waist portion of the diaper structure 20 onto the wearer's abdomen to fold and align the center of the front waist band along the symmetry plane of the wearer. The third alignment indicator may be on either the outer surface 37, the body-facing surface 41, or both surfaces of the diaper structure 20.

When the diaper structure 20 is donned as illustrated in FIG. 8, the first reference points 83 and 85 will be positioned to optically align the second reference points 111 and 113, which represent the visual intersection between the wearer's legs 102 and buttocks 104 from the perspective of the caregiver when baby 100 is in the above-described diaper changing position. By optically aligning the first reference points 81 and 83 with the second reference points 111 and 113, the position of diaper 20 is longitudinally and laterally optimized. The diaper 20 is then closed and fastened in that position.

The diapering process suitably has three discrete steps to avoid having to juggle multiple alignment features at once on the baby. The first step is to have the caregiver identify the lateral center near the back waistband edge 53, for example by locating the midpoint between the facing edges of the colored alignment indicators 81a and grasping the back waistband edge 53 near this point. The back waist region 24 is then slid under the baby in a fashion to keep the center of the back waist edge 53 very near the symmetry plane of the baby. In step two, the caregiver can now focus on stopping the sliding motion when the alignment indicator 75 meets the edge of the buttocks 106. The third step is to have the caregiver identify the center of the front waistband edge 51 by locating the midpoint between the facing edges of the alignment indicators 81a and grasping the front waistband edge 51 near this point. The front waist region 22 is then folded over along the symmetry plane of the baby generally toward or over the belly button. Alignment is now complete and the fasteners can be engaged for a perfect fit. In this process the caregiver has only one activity to focus on at a time and does not have to align multiple points on the diaper to multiple points on the baby at the same time. This saves time for the caregiver and increases the ease of use over conventional diapers.

A unique feature of this three-step process is that identifying the center of the back waist edge 53 and the center of the front waist edge 51 may be done by feel allowing the caregiver to focus on watching and controlling the baby during the first and third steps. More particularly, the diaper 20 may include additional alignment features at the centers of the front and back waist edges 51, 53. This feature allows the diaper of the invention to have two different sensory alignment features in discretely different locations on the diaper. Examples of suitably alignment features at the centers of the front and back waist edges 51, 53 include alignment features having a texture, thickness or other method to stimulate the touch sense, including temperature or moisture changes to identify the center near the front or back waistband edges 51, 53.

Figure 5:
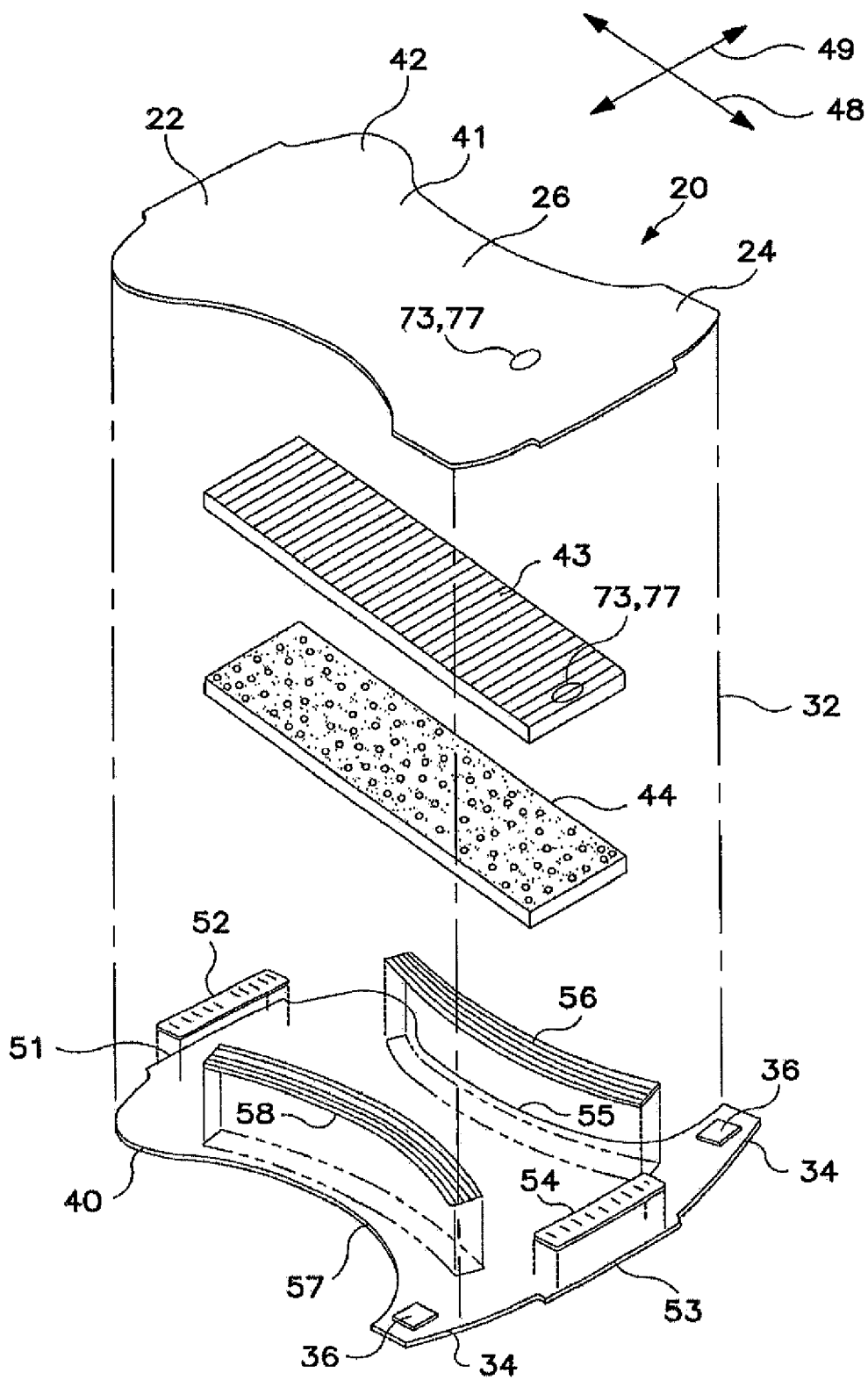

FIG. 5 illustrates an alternative embodiment of diaper structure 20 in which the alignment indicator 73 is shown as a single visually discernible first reference point 77 on the surge layer 43 and/or the body side liner 42. In the simplest form of the invention, an alignment indicator defining a single first reference point is all that is needed. The first reference point 77 can be represented as a visually discernible color, pattern, texture, protrusion, opening or other form. To don the diaper 20 in its optimal position, the first reference point 77 is positioned to optically align with the second reference point 107 on the baby 100 (FIG. 8), which is the back end of crevice 106 between buttocks 104.

The location of one or more second reference points on the wearer may also vary. Possible alternative second reference points include without limitation waste exit ports of the anus and genitalia, the perineal region, the bottom of the spine, or any other anatomical region covered by the diaper structure 20 when the diaper is on the wearer. Alternatively, the second reference point may be outside the region covered by the diaper, such as, for example, along the symmetry plane of the baby.

FIG. 6 illustrates the optimal positioning of alignment indicator 75 described with respect to FIGS. 2-5 and alignment indicators 81 similar to those described with respect to FIG. 4, on a diaper structure 20. In the embodiment of FIG. 6, the alignment indicator 75 is defined by the back edge 71 of colored surge layer 43, and includes a first reference point 77 at its center. The alignment indicators 81a are defined by the inside edges of longitudinally extending colored bands 81 on the body side liner. Laterally extending alignment indicator 75 is perpendicular to longitudinally extending alignment indicators 81a. Additional first reference points 83 and 85 are defined by the intersections of alignment indicators 75 and 81a or (if they do not intersect) by the positions where alignment indicators 75 and 81a extend very close to each other.

The distance "A" is the longitudinal distance from the back edge 53 of the diaper structure 20 to the laterally extending alignment indicator 75. The distance "D" is the longitudinal distance from the back edge 53 to the front edge 51 of the diaper structure 20. The distance "B" is the lateral distance from the first side edge 37 of the front waist region 22 to the first (nearest) longitudinally extending alignment indicator 81a. The distance "C" is the lateral distance from the second side edge 39 of the front waist region 22 to the second (nearest) longitudinally extending alignment indicator 81a.

Because diaper structures 20 come in various sizes and lengths, the location of laterally extending alignment indicator 75 can best be described as a ratio of the distance "D" (from the back edge to the front edge of the diaper) to the distance "A" (from the back edge of the diaper to the alignment indicator). Depending on the location of the selected second reference point, the ratio D/A may range from about 1.75 to about 3, suitably about 1.86 to about 2.77, particularly about 2 to about 2.55, or about 2.1 to about 2.4. To practice the method described with respect to FIG. 8, the ratio D/A can be about 2.23.

Variability is an integral part of this invention. All products are expected to deliver excellent fit. It is expected that all or most products produced fit a range of variability to effectively and consistently deliver the desired fit. Furthermore, it is expected that the D/A ratio vary by not more than 30% in a case of product (4 packages) to deliver the ease of use benefit.

The precise location of longitudinally extending alignment indicators 81a depends on the locations of the selected first reference points 83 and 85, and second reference points which correspond to these alignment indicators. However, for optimal lateral alignment, the distance "B" (from the lateral edge 37 to the first longitudinal alignment indicator 81a) should be within about ±10 mm of the distance "C" (from the lateral edge 39 to the second longitudinal alignment indicator 81a). Suitably, the distance "B" should be within about ±5 mm of the distance "C." In particular, the distances "B" and "C" may be about equal.

Regardless of their locations, the alignment indicators (e.g., 75 and 81a) should be visible from the body-facing surface of the diaper structure 20, and are suitably visible from the body-facing surface of the chassis 32, which is the region including the body side liner, outer cover and absorbent core. In the embodiment of FIG. 6, the front edge 69 of the surge layer 43 corresponds to the front edge of the colored region, and does not constitute an alignment indicator. In an alternative embodiment, the surge layer 43 may be colored along only part of its length (e.g., along a minor portion of its length), and the front edge of the colored region may constitute a laterally extending alignment indicator. In certain embodiments, the surge layer 43 or absorbent core 44 may include pulsed colored superabsorbent material that can be registered when injected to deliver an area that has color as an indicator.

Figure 7:
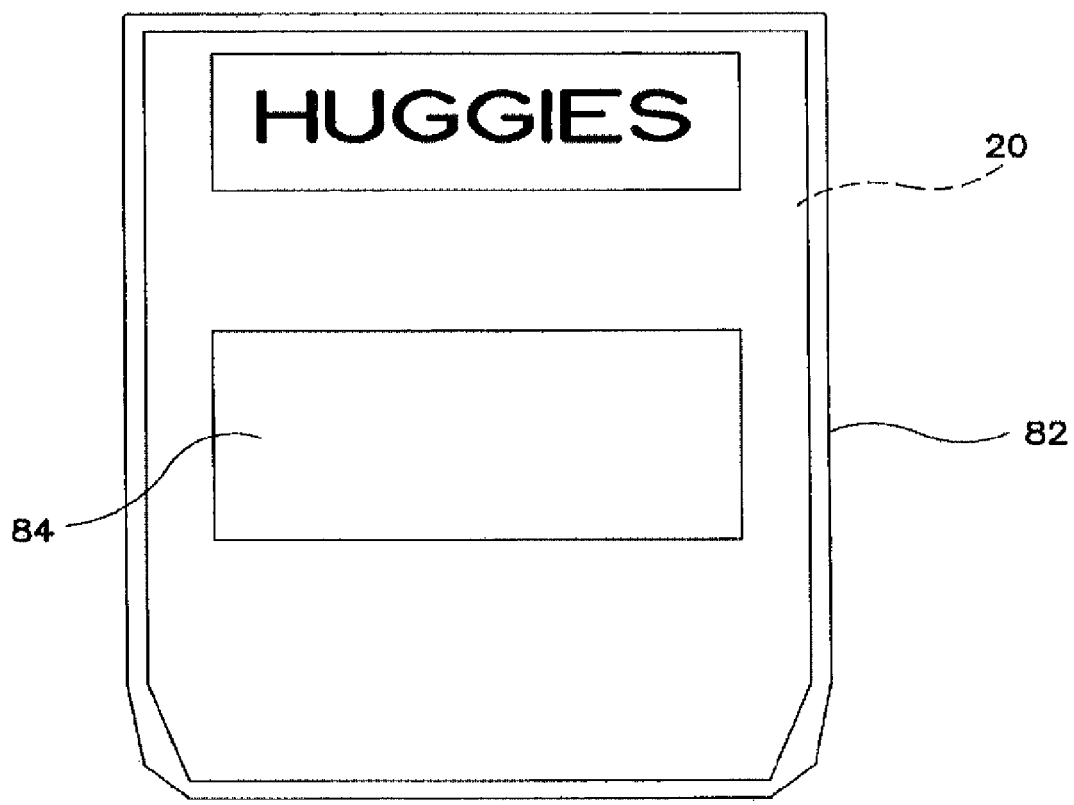
FIG. 7 is a plan view of a combination of one or more diaper structures and a package, wherein the diaper structures are in the package, and donning instructions are on or in the package.

In order for the diaper structure 20 to be used effectively by consumers, especially new consumers, instructions should be provided along with the diaper structure 20. The instructions may be written and/or graphical, and may be provided on a diaper structure package, as a separate insert in a diaper package, through in-store or media advertising, or other advertising channels not in direct contact with the diaper structure, or, in some instances, on the diaper structure itself. FIG. 7 illustrates a plan view of a package 82 in combination with one or more diaper structures 20 sold under the trade name HUGGIES. The package includes a label 84 which may be provided with instructions. The instructions may be in written form and may be in English, Spanish, French, Chinese, Japanese, German or any other language. The instructions may alternatively be in the form of graphics, possibly in combination with written instructions, which visually demonstrate the donning of diaper structure 20 on a wearer. Graphic changes on the product may not make it intuitive for the caregiver to use the graphics to align the product. This is why it is important to inform the caregiver of the benefit of the graphics and how to use alignment indicators. This is even more important when there is more than one alignment indicator and/or other graphic patterns on the diaper structure 20.

The instructions should be sufficient to guide the consumer on how to practice the method of the invention. The instructions should identify the locations of one or more visually discernible alignment indicators on the diaper structure which define the locations of one or more first reference points. The instructions should identify the locations of one or more second reference points on the wearer, instruct the consumer to place the diaper structure in a position where the one or more first reference points optically align with the one or more second reference points, and instruct the consumer to fasten the diaper structure in the position. For example, the instructions could describe the three-step process described above.

The method of the invention can be practiced with any absorbent garment and is not limited to diaper structures. In one embodiment, the method of donning an absorbent article includes the steps of defining a first reference point on a body-facing surface of the absorbent garment, defining a second reference point on a wearer, placing the absorbent garment in a position relative to the wearer where the first reference point optically aligns with the second reference point, and fastening the absorbent garment in the position. In a related embodiment, the foregoing method includes the steps of defining a plurality of first reference points on a body-facing surface of the absorbent garment, defining a plurality of second reference points on a wearer, placing the absorbent garment in a position relative to the wearer where the first reference points optically align with the second reference points, and fastening the absorbent garment in the position.

The invention is also directed to a method of facilitating the donning of an absorbent garment on a wearer. The method includes the steps of defining one or more first reference points on a body-facing surface of the absorbent garment, defining one or more second reference points on a prospective wearer, and instructing a consumer to place the absorbent garment in a position relative to the wearer where the one or more first reference points optically align with the one or more second reference points. The consumer can then be instructed to fasten the absorbent garment in the position.

For the sake of completeness, the following discussion is directed mainly to conventional features of the diaper structure 20 described above. The absorbent chassis 32 includes body side liner 42, surge layer 43, absorbent core 44 and outer cover 40.

The liquid permeable body side liner 42 is illustrated as overlying the outer cover 40, absorbent core 44 and surge layer 43, and may but need not have the same dimensions as the outer cover 40. The body side liner 42 is desirably compliant, soft feeling, and non-irritating to the wearer's skin. Further, the body side liner 42 can be less hydrophilic than the absorbent core 44, to present a relatively dry surface to the wearer and permit liquid to readily penetrate through its thickness. The body side liner 42 desirably includes a material that can be elastic, stretchable, extensible, non-stretchable, or non-extensible.

The body side liner 42 can be manufactured from a wide selection of web materials, such as synthetic fibers (for example, polyester or polypropylene fibers), natural fibers (for example, wood or cotton fibers), a combination of natural and synthetic fibers, porous foams, reticulated foams, apertured plastic films, or the like. Various woven and nonwoven fabrics can be used for the body side liner 42. For example, the body side liner can be composed of a meltblown or spunbonded web of polyolefin fibers. The body side liner can also be a bonded-carded web composed of natural and/or synthetic fibers. The body side liner can be composed of a substantially hydrophobic material, and the hydrophobic material can, optionally, be treated with a surfactant or otherwise processed to impart a desired level of wettability and hydrophilicity. For example, the material can be surface treated with about 0.45 weight percent of a surfactant mixture including AHCOVEL® N-62 available from Uniqema Inc., a division of ICI of New Castle, Del., U.S.A. and GLUCOPON® 220UP available from Cognis Corporation of Ambler, Pa., and produced in Cincinnati, Ohio, in an active ratio of 3:1. The surfactant can be applied by any conventional means, such as spraying, printing, brush coating or the like. The surfactant can be applied to the entire body side liner 42 or can be selectively applied to particular sections of the body side liner, such as the medial section along the longitudinal centerline.

A suitable liquid permeable body side liner 42 is a nonwoven bicomponent web having a basis weight of about 27 gsm. The nonwoven bicomponent can be a spunbond bicomponent web, or a bonded carded bicomponent web. Suitable bicomponent staple fibers include a polyethylene/polypropylene bicomponent fiber available from CHISSO Corporation, Osaka, Japan. In this particular bicomponent fiber, the polypropylene forms the core and the polyethylene forms the sheath of the fiber. Other fiber orientations are possible, such as multi-lobe, side-by-side, end-to-end, or the like. While the outer cover 40 and body side liner 42 can include extendible and/or elastomeric materials, it can be desirable in some embodiments for the composite structure to be generally inelastic, where the outer cover, body side liner, absorbent core and surge layer include materials that are generally not elastomeric.

The surge layer 43 is formed of a highly liquid pervious, open, porous material. Suitable materials include without limitation porous woven materials, porous nonwoven materials, apertured woven or nonwoven materials, open-celled foams, curly cellulose fiber mat, and batting. Examples include flexible porous sheets of thermoplastic fibers such as polypropylene, polyethylene or polyester fibers; webs of spunbond polypropylene, polyethylene or polyester fibers; webs of rayon fibers; bonded carded webs of synthetic or natural fibers or combinations thereof. U.S. Pat. No. 5,904,675, issued May 18, 1999 to Laux et al., provides further examples of suitable surge materials. This patent is incorporated by reference.

The absorbent core 44 can be any structure which is generally compressible, conformable, non-irritating to the wearer's skin, and capable of absorbing and retaining liquids and certain body wastes at anticipated levels despite the narrowed crotch width. The absorbent core 44 can be manufactured in a wide variety of sizes and shapes, and from a wide variety of liquid absorbent materials commonly used in the art. For example, the absorbent core 44 can suitably include a matrix of hydrophilic fibers, such as a web of cellulosic fluff, mixed with particles of a high-absorbency material commonly known as superabsorbent material. In a particular embodiment, the absorbent core 44 includes a matrix of cellulosic fluff, such as wood pulp fluff, and superabsorbent hydrogel-forming particles. The wood pulp fluff can be exchanged with synthetic, polymeric, meltblown fibers or with a combination of meltblown fibers and natural fibers. The superabsorbent particles can be substantially homogeneously mixed with the hydrophilic fibers or can be nonuniformly mixed. The fluff and superabsorbent particles can also be selectively placed into desired zones of the absorbent core 44 to better contain and absorb body exudates. The absorbent core 44 can have variable thickness, with greater thickness in "target" areas, such as in a central portion of the crotch region. The concentration of the superabsorbent particles can also vary through the thickness of the absorbent core 44. Alternatively, the absorbent core 44 can include a laminate of fibrous webs and superabsorbent material or other suitable means of maintaining a superabsorbent material in a localized area. The absorbent core 44 may or may not be wrapped or encompassed by a suitable tissue wrap that maintains the integrity and/or shape of the absorbent core 44. In certain embodiments, the absorbent core 44 may contain a body side liner and/or a moisture barrier in addition to absorbent and distribution elements. In such embodiments, the absorbent core 44 may be attached to the outer cover 40 and need not be sandwiched between two layers. The absorbent core 44 may also contain leg elastics in embodiments such as this.

Suitable superabsorbent materials can be selected from natural, synthetic, and modified natural polymers and materials. The superabsorbent materials can be inorganic materials, such as silica gels, or organic compounds, such as crosslinked polymers. Suitable superabsorbent materials are available from various commercial vendors, such as Dow Chemical Company located in Midland, Mich., U.S.A., and Degussa Superabsorber in Greensboro, N.C., U.S.A. Typically, a superabsorbent material is capable of absorbing at least about 15 times its weight in water, and desirably is capable of absorbing more than about 25 times its weight in water.

The outer cover 40 desirably includes a material that may be substantially liquid impermeable or liquid permeable, and can be elastic, stretchable, extensible, non-stretchable, or non-extensible. The outer cover 40 can be a single layer of liquid impermeable material, but desirably includes a multilayered laminate structure in which at least one of the layers is liquid impermeable. For instance, the outer cover 40 can include a liquid permeable outer layer and a liquid impermeable inner layer that are suitably joined together by a laminate adhesive (not shown). Suitable laminate adhesives, which can be applied continuously or intermittently as beads, a spray, parallel swirls, or the like, can be obtained from Findley Adhesives, Inc., of Wauwatosa, Wis., U.S.A., or from National Starch and Chemical Company, Bridgewater, N.J., U.S.A. The liquid permeable outer layer can be any suitable material and desirably one that provides a generally cloth-like texture. One example of such a material is a 20 gsm (grams per square meter) spunbond polypropylene nonwoven web. The outer layer may also be made of those materials of which liquid permeable body side liner 42 is made. While it is not a necessity for the outer layer to be liquid permeable, it is desired that it provides a relatively cloth-like texture to the wearer.

The inner layer of the outer cover 40 can be both liquid and vapor impermeable, or can be liquid impermeable and vapor permeable. The inner layer of the outer cover 40 desirably includes a material that can be elastic, stretchable, extensible, non-stretchable, or non-extensible. The inner layer is desirably manufactured from a thin plastic film, although other flexible liquid impermeable materials may also be used. The inner layer, or the liquid impermeable outer cover 40 when a single layer, prevents waste material from wetting articles, such as bedsheets and clothing, as well as the wearer and care giver. A suitable liquid impermeable film for use as a liquid impermeable inner layer, or a single layer liquid impermeable outer cover 40, is a 0.02 millimeter polyethylene film commercially available from Huntsman Packaging of Newport News, Va., U.S.A. If the outer cover 40 is a single layer of material, it can be embossed and/or matte finished to provide a more cloth-like appearance. As earlier mentioned, the liquid impermeable material can permit vapors to escape from the interior of the disposable absorbent article, while still preventing liquids from passing through the outer cover 40. A suitable "breathable" material is composed of a microporous polymer film or a nonwoven fabric that has been coated or otherwise treated to impart a desired level of liquid impermeability. A suitable microporous film is a PMP-1 film material commercially available from Mitsui Toatsu Chemicals, Inc., Tokyo, Japan, or an XKO-8044 polyolefin film commercially available from 3M Company, Minneapolis, Minn.

Certain "non-breathable" elastic films can also be used to make the outer cover 40. Examples of suitable non-breathable films can be made of styrene-ethylene-butylene-styrene or styrene-isoprene-styrene block copolymers, KRATON® polymers from Kraton Inc. of Houston, Tex., U.S.A., metallocene catalyzed elastomers or plastomers, and the like. Other materials suitable for making the outer cover 40 include monolithic breathable films, such as those made of polyether amide based polymers, for example PEBAX, and ether/ester polyurethane thermal-plastic elastomers.

The absorbent chassis 32 may also incorporate other conventional materials and layers. A vapor-permeable, hydrophobic spacer layer (not shown) may be positioned between the absorbent core 44 and the outer cover 40 as a further measure to prevent a clammy feeling on an outer surface of the outer cover 40 when the diaper structure is loaded.

The diaper 20 may include a waist elastic member 52 and 54 in the front waist region 22, in the back waist region 24, or in both the front and back waist regions 22, 24 of the garment, operatively attached to the outer cover 40 and/or body side liner 42 and extending across part or a full length of the waist regions.

As explained above, to further enhance containment and/or absorption of body exudates, the diaper 20 may also include leg elastic members 56 and 58, as are known to those skilled in the art. The leg elastic members 56 and 58 may be operatively joined to the outer cover 40 and/or body side liner 42 along opposite side edges of the absorbent chassis 32 and positioned in the crotch region 26 of the diaper 20.

The waist elastic members 52 and 54, and the leg elastic members 56 and 58, can be formed of any suitable elastic material. As is well known to those skilled in the art, suitable elastic materials include sheets, strands or ribbons of natural rubber, synthetic rubber, or thermoplastic elastomeric polymers. The elastic materials can be stretched and adhered to a substrate, adhered to a gathered substrate, or adhered to a substrate and then elasticized or shrunk, for example with the application of heat; such that elastic constrictive forces are imparted to the substrate. In one particular embodiment, for example, the waist elastic members 52 and 54 may include a polystyrene-polyethylene-polypropylene-polystyrene (SEPS) block copolymer, such as KRATON® G2760, available from Kraton Inc. of Houston, Tex., U.S.A.

The diaper 20 may be refastenable, thereby including a refastenable fastening system for securing the diaper about the waist of the wearer. One example of a suitable refastenable fastening system includes fastening components 36, such as hook components, located along or adjacent to the distal edges of the tabs 34. Suitable single-sided hook materials are available from Velcro Industries B.V., Amsterdam, Netherlands, or affiliates thereof. The fastening components 36 are adapted to refastenably connect to one or more mating fastening components 38, such as loop material, located on an outer surface 37 of the front waist region 22. One example of suitable loop material is "point unbonded" material. Point unbonded materials are fabrics having continuous thermally bonded areas defining a plurality of discrete unbonded areas and are described in greater detail in U.S. Pat. No. 5,858,515 issued Jan. 12, 1999 to Stokes, et al., incorporated herein by reference. The engaging elements of the fastening components 36 are adapted to repeatedly engage and disengage the engaging elements of the mating fastening components 38.

Additionally, the diaper 20 may include a pre-fastened, non-refastenable second fastening system (not shown) to assist in applying the diaper 20 to a wearer. The non-refastenable fastening system may be torn when removing the diaper 20 from the wearer. The non-refastenable fastening system may be formed by attaching one edge of a loop material to a distal edge of the front waist region 22 of the absorbent chassis 32 and attaching an opposite edge of the same material to the tab 34 on the same side in the back waist region 24 of the garment with releasable bonds. Alternatively, the loop material may extend across a full width of the front waist region 22 of the absorbent chassis 32, thereby providing a mating fastening component 38, or landing strip, for the fastening components 36 of the refastenable fastening system, and extend even farther past the distal edges of the front waist region 22, such that the non-refastenable fastening system can be formed from the loop material that extends past the distal edges of the front waist region.

To enhance containment and/or absorption of any body exudates discharged from the wearer, the chassis 32 may include a pair of elasticized containment flaps (not shown) which are configured to provide a barrier to the transverse flow of body exudates. Elastic containment flaps typically define an unattached edge which assumes an upright, generally perpendicular configuration in at least the crotch region 26 of the diaper 20 to form a seal against the wearer's body. The containment flaps can be located along the transversely opposed side edges of the chassis 32, or in the crotch region 26, and can extend longitudinally along the entire length of the chassis or may only extend partially along the length of the chassis. Suitable constructions and arrangements for containment flaps are generally well known to those skilled in the art.

As described herein, the various components of the absorbent garment 20 can be integrally assembled together employing various types of suitable attachment means, such as adhesive, sonic and thermal bonds or combinations thereof.

The absorbent garments can be packaged individually, or multiple absorbent garments can be packaged together in suitable packaging, such as in bags or boxes constructed of paper or polymeric film, for example. A package 82 (FIG. 7) may contain any number of absorbent garments 20. The absorbent garments may be stacked so that each adjacent pair of garments contacts one another along a planar portion of their outer covers. These stacks may be packaged together such that a package contains multiple stacks of absorbent garments.

EXAMPLES

Two sample diapers were formed in accordance with the invention. Both diapers were formed from the same materials as in HUGGIES Ultratrim Step 4 diapers, available from Kimberly-Clark Corporation of Neenah, Wis., and differed only by the specifications described below.

The first sample diaper included blue containment flaps having the alignment indicators 81 spaced apart by 1 inch (2.54 cm) at the back and front waist bands, and an aqua surge layer positioned 190 mm from the back waist edge. Total length of the diaper was 425 mm.

The second sample diaper included an embossed pattern at the front and back waistband edges with an aqua surge layer positioned 190 mm from the back waist edge. Total length of the diaper was 425 mm. The embossed pattern also serves as an aid for grasping and holding onto the diaper while diapering. The embossed pattern was embossed with a pressured patterned roll against an anvil roll. The pattern was 1 inch in lateral width.

While the embodiments of the invention described herein are presently preferred, various modifications and improvements can be made without departing from the spirit and scope of the invention. The scope of the invention is indicated by the appended claims, and all changes that fall within the meaning and range of equivalents are intended to be embraced therein.

What is claimed is:

1. A combination, comprising:
at least one diaper structure;
a package enclosing the diaper structure; and
instructions defining one or more first reference points on the diaper structure, one or more second reference points on a prospective wearer, and directing a consumer to place the diaper structure in a position relative to the wearer so that the one or more first reference points optically align with the one or more second reference points;
wherein the diaper structure comprises one or more visually discernible alignment indicators visible from a body-facing surface of the diaper structure, and including the one or more first reference points;
wherein the diaper structure comprises a surge layer having a visually contrasting color, and the surge layer comprises the alignment indicator.

2. A combination, comprising:
at least one absorbent garment;
a package enclosing the absorbent garment; and
instructions defining one or more first reference points on the absorbent garment, one or more second reference points on a prospective wearer, and directing a consumer to place the absorbent garment in a position relative to the wearer so that the one or more first reference points optically align with the one or more second reference points;
wherein the absorbent garment comprises one or more visually discernible alignment indicators visible from a body-facing surface of the absorbent garment, and including the one or more first reference points;
wherein the absorbent garment comprises an absorbent layer including colored superabsorbent material, and the colored superabsorbent material comprises the alignment indicator.

3. A combination, comprising:
at least one absorbent garment;
a package enclosing the absorbent garment; and
instructions defining one or more first reference points on the absorbent garment, one or more second reference points on a prospective wearer, and directing a consumer to place the absorbent garment in a position relative to the wearer so that the one or more first reference points optically align with the one or more second reference points;
wherein the absorbent garment comprises one or more visually discernible alignment indicators visible from a body-facing surface of the absorbent garment, and including the one or more first reference points;
wherein the absorbent garment comprises a waist elastic having a visually contrasting pattern or color, and the waist elastic comprises the alignment indicator.

4. A combination, comprising:
at least one absorbent garment;
a package enclosing the absorbent garment; and
instructions defining one or more first reference points on the absorbent garment, one or more second reference points on a prospective wearer, and directing a consumer to place the absorbent garment in a position relative to the wearer so that the one or more first reference points optically align with the one or more second reference points;
wherein the absorbent garment comprises one or more tactically discernible alignment indicators on a surface of the absorbent garment.

5. A combination, comprising:
at least one diaper structure;
a package enclosing the diaper structure; and
instructions defining one or more first reference points on the diaper structure, one or more second reference points on a prospective wearer, and directing a consumer to place the diaper structure in a position relative to the wearer so that the one or more first reference points optically align with the one or more second reference points;
wherein the diaper structure having:
a front edge, back edge and side edges;
a front waist region, a back waist region, and fasteners configured to secure the diaper structure on a wearer after manual adjustment to position the diaper structure relative to the wearer;
a liquid-permeable body side liner having a body-facing surface;
an outer cover;
an absorbent core between the body side liner and the outer cover; and
a first alignment indicator visible from the body-facing surface and having a visually discernible feature, wherein the first alignment indicator identifies a particular longitudinal position on the diaper structure between the front edge and the back edge of the diaper structure, the first alignment indicator disposed to be optically aligned with a reference point on a prospective wearer as the diaper structure is donned on the wearer and to remain visible after the diaper structure is at an optimal position on the wearer;
wherein the first alignment indicator is a longitudinal distance "A" from the back edge, and the front edge is a longitudinal distance "D" from the back edge; and the first alignment indicator is positioned such that a ratio of D/A is about 1.75 to about 3.

* * * * *